US010568623B2

(12) United States Patent
Cappola et al.

(10) Patent No.: US 10,568,623 B2
(45) Date of Patent: *Feb. 25, 2020

(54) SURGICAL INSTRUMENT AND BUSHING

(71) Applicant: Covidien LP, Mansfield, MA (US)

(72) Inventors: Kenneth M. Cappola, Monroe, CT (US); Lee Ann Olson, Wallingford, CT (US); Frank C. Maffei, Shelton, CT (US)

(73) Assignee: COVIDIEN LP, Mansfield, MA (US)

( * ) Notice: Subject to any disclaimer, the term of this patent is extended or adjusted under 35 U.S.C. 154(b) by 615 days.

This patent is subject to a terminal disclaimer.

(21) Appl. No.: 15/296,477

(22) Filed: Oct. 18, 2016

(65) Prior Publication Data
US 2017/0035416 A1    Feb. 9, 2017

Related U.S. Application Data

(63) Continuation of application No. 13/871,233, filed on Apr. 26, 2013, now Pat. No. 9,468,439.
(Continued)

(51) Int. Cl.
A61B 17/068    (2006.01)
A61B 17/072    (2006.01)
(Continued)

(52) U.S. Cl.
CPC ...... *A61B 17/068* (2013.01); *A61B 17/07207* (2013.01); *A61B 2017/00464* (2013.01);
(Continued)

(58) Field of Classification Search
CPC .......... A61B 17/068; A61B 2017/2946; A61B 17/072
(Continued)

(56) References Cited

U.S. PATENT DOCUMENTS 5,865,361 A    2/1999    Milliman et al.
6,032,849 A    3/2000    Mastri et al.
(Continued)

FOREIGN PATENT DOCUMENTS

CA    2790909 A1    4/2013
EP    2090253 A2    8/2009
(Continued)

OTHER PUBLICATIONS

Japanese Office Action dated Mar. 31, 2017 issued in corresponding JP Application No. 2013-122860.
(Continued)

*Primary Examiner* — Michelle Lopez
(74) *Attorney, Agent, or Firm* — Carter, DeLuca & Farrell LLP

(57) ABSTRACT

A surgical instrument comprising a handle assembly, and actuation member, an elongated body portion, and a locking mechanism is disclosed. The locking mechanism is disposed in mechanical cooperation with the actuation member, and is configured to substantially prevent at least a partial movement of the actuation member when the elongated body portion is not engaged with a loading unit. The locking mechanism comprises a link, a bushing, and a connecting member. The link is configured for mechanical engagement with a portion of a loading unit. At least a portion of the busing is disposed proximally of at least a portion of the link. At least a portion of the connecting member is disposed proximally of at least a portion of the bushing. Engagement between a loading unit and the elongated body portion causes proximal movement of the link, the bushing, and the connecting member.

20 Claims, 10 Drawing Sheets

Related U.S. Application Data

(60) Provisional application No. 61/666,028, filed on Jun. 29, 2012.

(51) Int. Cl.
*A61B 17/29* (2006.01)
*A61B 17/00* (2006.01)

(52) U.S. Cl.
CPC ............ *A61B 2017/00526* (2013.01); *A61B 2017/2946* (2013.01)

(58) Field of Classification Search
USPC ..................................... 227/175.1
See application file for complete search history.

(56) References Cited

U.S. PATENT DOCUMENTS

| | | | |
|---|---|---|---|
| 7,815,090 | B2 | 10/2010 | Marczyk |
| 7,815,091 | B2 | 10/2010 | Marczyk |
| 7,819,296 | B2 | 10/2010 | Hueil et al. |
| 7,819,297 | B2 | 10/2010 | Doll et al. |
| 7,819,298 | B2 | 10/2010 | Hall et al. |
| 7,861,906 | B2 | 1/2011 | Doll et al. |
| 7,866,527 | B2 | 1/2011 | Hall et al. |
| 7,959,051 | B2 | 6/2011 | Smith et al. |
| 7,980,443 | B2 | 7/2011 | Scheib et al. |
| 9,468,439 | B2 * | 10/2016 | Cappola ............ A61B 17/07207 |
| 2004/0232201 | A1 * | 11/2004 | Wenchell ......... A61B 17/07207 227/176.1 |
| 2009/0206131 | A1 | 8/2009 | Weisenburgh, II et al. |
| 2009/0206132 | A1 | 8/2009 | Hueil et al. |
| 2009/0206133 | A1 | 8/2009 | Morgan et al. |
| 2009/0206137 | A1 | 8/2009 | Hall et al. |
| 2011/0006099 | A1 | 1/2011 | Hall et al. |
| 2011/0068148 | A1 | 3/2011 | Hall et al. |
| 2011/0132962 | A1 | 6/2011 | Hall et al. |
| 2011/0132964 | A1 | 6/2011 | Weisenburgh, II et al. |
| 2014/0001233 | A1 | 1/2014 | Cappola et al. |

FOREIGN PATENT DOCUMENTS

| | | |
|---|---|---|
| EP | 2090254 A1 | 8/2009 |
| EP | 2583630 A2 | 4/2013 |
| WO | WO99/15086 | 4/1999 |
| WO | 03030743 A2 | 4/2003 |

OTHER PUBLICATIONS

Canadian Office Action dated Mar. 21, 2019, issued in CA Appln. No. 2,815,624.
European Search Report EP 13 17 4200 dated Oct. 4, 2013.

* cited by examiner

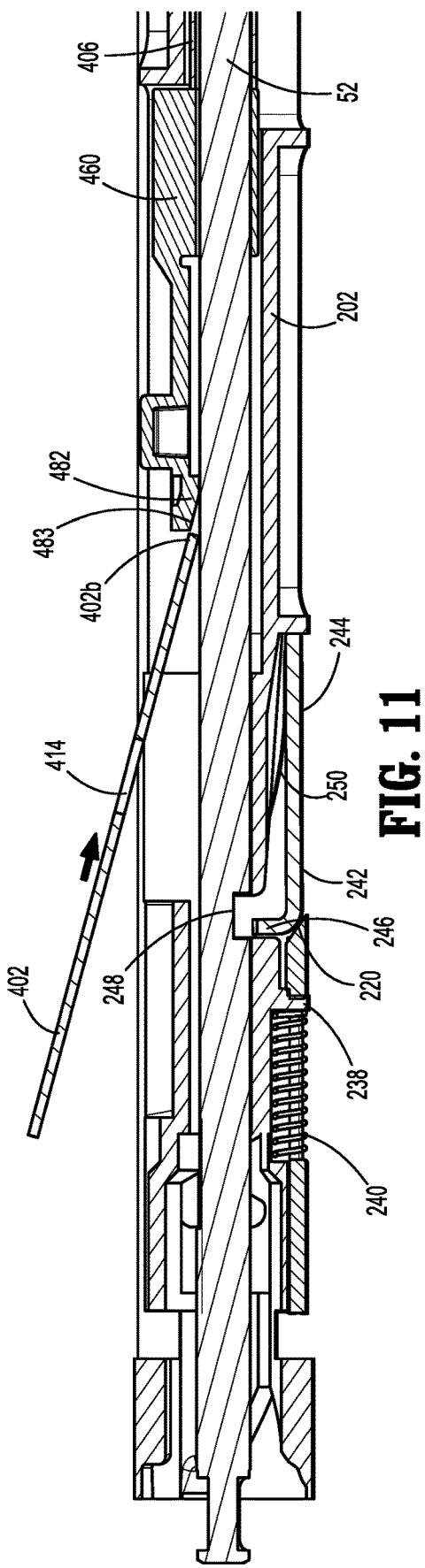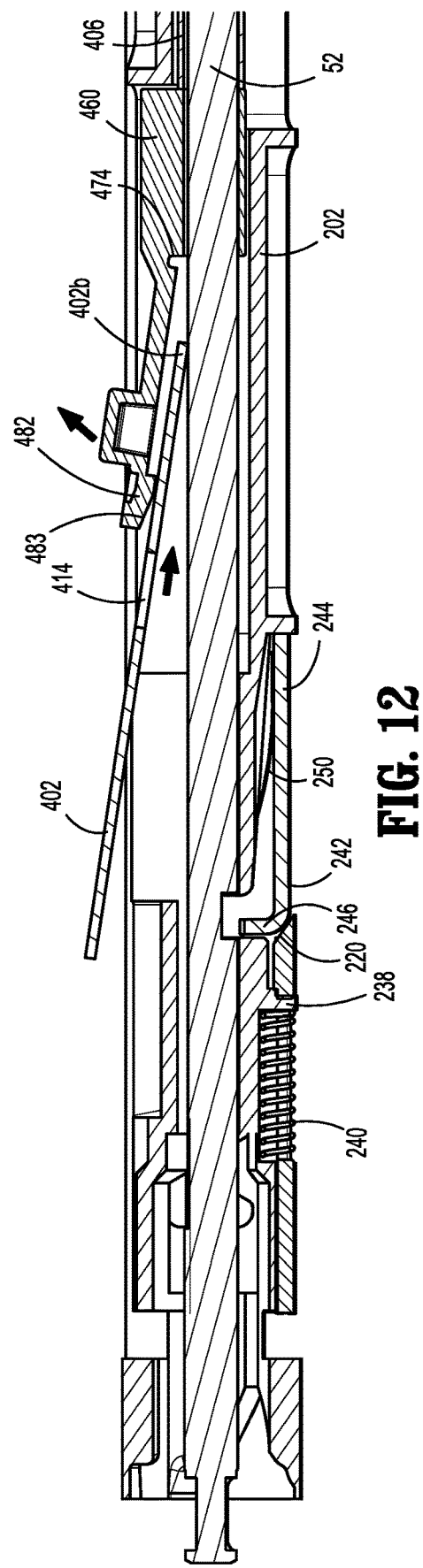

SURGICAL INSTRUMENT AND BUSHING

CROSS-REFERENCE RELATED APPLICATIONS

This application is a continuation of U.S. patent application Ser. No. 13/871,233, filed Apr. 26, 2013, which claims the benefit of and priority to U.S. Provisional Patent Application Ser. No. 61/666,028, filed Jun. 29, 2012, the entire disclosure of which is incorporated by reference herein.

BACKGROUND

Technical Field

This application relates to a surgical instrument, and more particularly, to an endoscopic surgical fastening instrument having a loading unit for applying a plurality of surgical fasteners to body tissue, and to a bushing for use with the surgical instrument.

Background of Related Art

Various types of surgical instruments used to surgically join tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument, which may include an anvil assembly, a cartridge assembly for supporting an array of surgical staples, an approximation mechanism for approximating the cartridge and anvil assemblies, and a firing mechanism for ejecting the surgical staples from the cartridge assembly.

Using a surgical stapling instrument, it is common for a surgeon to approximate the anvil and cartridge members. Next, the surgeon can fire the instrument to emplace staples in tissue. Additionally, the surgeon may use the same instrument or a separate instrument to cut the tissue adjacent or between the row(s) of staples.

SUMMARY

The present disclosure relates to a surgical instrument comprising a handle assembly, and actuation member, an elongated body portion, and a locking mechanism. The locking mechanism is disposed in mechanical cooperation with the actuation member, and is configured to substantially prevent at least a partial movement of the actuation member when the elongated body portion is not engaged with a loading unit. The locking mechanism comprises a link, a bushing, and a connecting member. The link is disposed at least partially within the elongated body portion and is configured for mechanical engagement with a portion of a loading unit. At least a portion of the busing is disposed proximally of at least a portion of the link. At least a portion of the connecting member is disposed proximally of at least a portion of the bushing, and the connecting member is disposed in mechanical cooperation with the actuation member. Engagement between a loading unit and the elongated body portion causes proximal movement of the link, the bushing, and the connecting member.

In disclosed embodiments, a distal face of the bushing abuts a proximal end of the link.

In disclosed embodiments, a proximal face of the bushing abuts a distal end of the connecting member.

In disclosed embodiments, the surgical instrument further comprises a control rod disposed at least partially within the elongated body portion, such that longitudinal translation of the control rod effects a function of a loading unit when the loading unit is engaged with the elongated body portion. Here, control rod is longitudinally translatable with respect to the link, with respect to the bushing and with respect to the connecting member. It is also disclosed that the control rod is longitudinally translatable through an aperture in the bushing. It is further disclosed that the control rod is longitudinally translatable through the connecting member.

In disclosed embodiments, a transverse dimension of a contacting portion of a proximal surface of the bushing is between about 2 to about 10 times larger than a distal end of a wall of the connecting tube. It is also disclosed that a transverse dimension of a contacting portion of a distal surface of the bushing is between about 1 to about 3 times larger than a proximal end of the link.

The present disclosure also relates to a surgical instrument comprising a handle assembly, and actuation member, an elongated body portion, a loading unit, and a locking mechanism. The actuation member is disposed in mechanical cooperation with the handle assembly. The elongated body portion extends distally from the handle assembly and defines a longitudinal axis. The loading unit includes a proximal body portion and a tool assembly. The proximal body portion is configured for selective engagement with the elongated body portion. The locking mechanism is disposed in mechanical cooperation with the actuation member. The locking mechanism is configured to enable movement of the actuation member when the elongated body portion and the loading unit are engaged. The locking mechanism comprises a link, a bushing, and a connecting member. The link is disposed at least partially within the elongated body portion and is configured for mechanical engagement with a portion of the loading unit. At least a portion of the link is longitudinally translatable with respect to the elongated body portion. At least a portion of the busing is disposed proximally of at least a portion of the link. At least a portion of the bushing is longitudinally translatable with respect to the elongated body portion. At least a portion of the connecting member is disposed proximally of at least a portion of the bushing. The connecting member is disposed in mechanical cooperation with the actuation member. Engagement between the loading unit and the elongated body portion causes proximal movement of the link, proximal movement of the bushing, and proximal movement of the connecting member.

In disclosed embodiments, a distal face of the bushing abuts a proximal end of the link.

In disclosed embodiments, a proximal face of the bushing abuts a distal end of the connecting member.

In disclosed embodiments, the surgical instrument further comprises a control rod disposed at least partially within the elongated body portion, such that longitudinal translation of the control rod effects a function of the loading unit when the loading unit is engaged with the elongated body portion. Here, it is disclosed that the control rod is longitudinally translatable with respect to the link, with respect to the bushing and with respect to the connecting member. It is also disclosed that the control rod is longitudinally translatable through an aperture in the bushing. It is further disclosed that the control rod is longitudinally translatable through the connecting member.

In disclosed embodiments, a transverse dimension of a contacting portion of a proximal surface of the bushing is between about 2 to about 10 times larger than a distal end of a wall of the connecting tube. It is also disclosed that a transverse dimension of a contacting portion of a distal surface of the bushing is between about 1 to about 3 times larger than a proximal end of the link.

BRIEF DESCRIPTION OF THE DRAWINGS

Various embodiments of the present disclosure are described herein with reference to the drawings wherein:

FIGS. 11 and 12 are longitudinal cross-sectional views of a portion of the locking mechanism during different stages of assembly of a first link.

DETAILED DESCRIPTION

Figure 1:
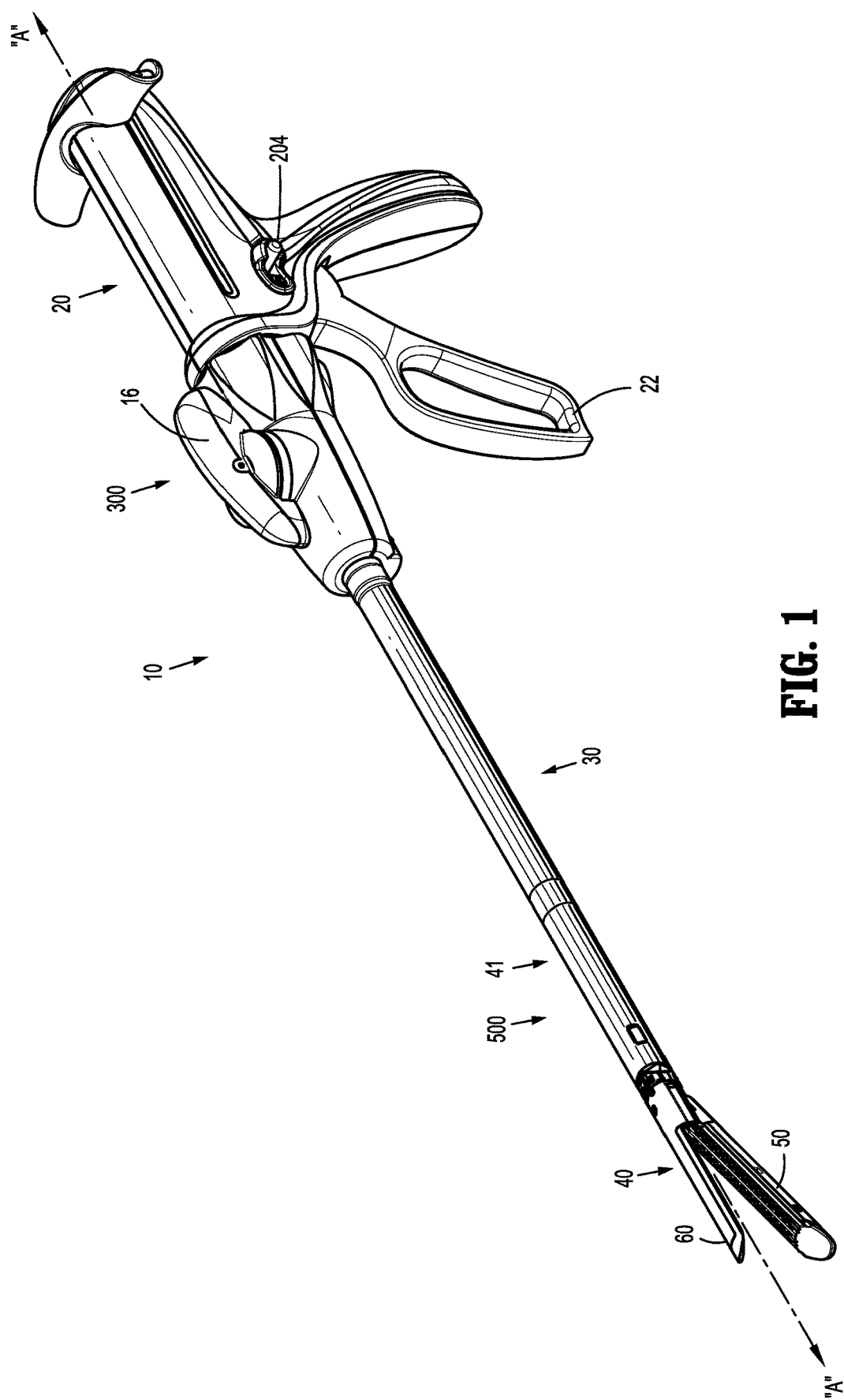
FIG. 1 is a front, perspective view of one embodiment of the presently disclosed surgical instrument including a loading unit engaged with an elongated body.

Embodiments of the presently disclosed surgical instrument, and bushing for use therewith, are described in detail with reference to the drawings, wherein like reference numerals designate corresponding elements in each of the several views. As is common in the art, the term "proximal" refers to that part or component closer to the user or operator, e.g., surgeon or physician, while the term "distal" refers to that part or component farther away from the user.

A surgical stapling instrument of the present disclosure is indicated as reference numeral 10 in FIG. 1. The depicted surgical instrument fires staples, but it may be adapted to fire any other suitable fastener such as clips and two-part fasteners. Additionally, while the figures depict a linear fastener-applying surgical instrument, other types of endoscopic surgical instruments are encompassed by the present disclosure and are usable with the disclosed bushing 460. For example, further details of endoscopic forceps are described in commonly-owned U.S. Patent Publication No. 2010/0179540 to Marczyk et al., and U.S. patent application Ser. No. 12/718,143 to Marczyk et al., the entire contents of each of which are hereby incorporated by reference herein. In another example, further details of a circular fastener-applying surgical instrument are described in commonly-owned U.S. Patent Publication No. 2009/0173767 to Milliman et al., the entire contents of which are hereby incorporated by reference herein.

Generally, surgical instrument 10 includes a handle assembly 20 including a movable handle 22, an elongated or endoscopic portion 30 extending distally from the handle assembly 20 and defining a longitudinal axis "A," and a loading unit 500 attachable to endoscopic portion 30, e.g., to allow surgical instrument 10 to have greater versatility. Loading unit 500 includes a proximal portion 41 and an end effector 40, including a cartridge 50 and an anvil 60, disposed adjacent the proximal portion 41. The loading unit 500 may be configured for a single use, and/or may be configured to be used more than once. Examples of loading units for use with a surgical stapling instrument are disclosed in commonly-owned U.S. Pat. No. 5,752,644 to Bolanos et al., the entire contents of which are hereby incorporated by reference herein.

The movable handle 22 is actuatable (e.g., through successive strokes) to cause distal advancement of a drive rod or control rod 52, such that the drive rod engages a portion of a drive assembly, which forces at least a portion of the drive assembly to translate distally. (Further details of how actuation of movable handle 22 causes distal advancement of the drive rod are explained in U.S. Pat. No. 6,953,139 to Milliman et al., which is hereby incorporated by reference herein.) Distal movement of the drive rod, and in particular, a dynamic clamping member engaged therewith, causes an actuation sled to move distally through the cartridge 50, which causes cam wedges of the actuation sled to sequentially engage pushers to move pushers vertically within retention slots and eject fasteners towards the anvil 60. Subsequent to the ejection of fasteners from the retention slots (and into tissue), a cutting edge of the dynamic clamping member severs the fastened tissue as the cutting edge travels distally through a slot of the cartridge 50.

With reference to FIGS. 4-12, instrument 10 also includes a locking mechanism 400 for preventing operation of instrument 10 before a loading unit 500 has been engaged with elongated portion 30 of instrument 10. Locking mechanism 400 includes a first link 402, a bushing 460, a connecting member or connecting tube 406, and an articulation locking member 408. Bushing 460 includes a body portion 470 and a finger 480 extending distally therefrom. First link 402 includes a plate-like member which is supported between control rod 52 and an inner body portion 232 of elongated portion 30 of the instrument 10 on a flat surface 53 which is .ground into control rod 52 (see FIG. 10). Additionally, first link 402 includes an engagement structure 414 (e.g., an opening, slot, detent, etc.) which is dimensioned to receive a tongue 482 depending from finger 480 of bushing 460. Bushing 460, link 402, and flat surface 53 on control rod 52 function together to prevent control rod 52 from rotating in outer tube 230. This ensures proper rotational alignment between a hook 242 within outer tube 230 and a notch 248 in control rod 52 (see FIG. 10, for example).

Body portion 470 of bushing 460 is disposed proximally of first link 402 and bushing 460 is radially positioned between outer tube 230 and release link 202. Additionally, body portion 470 of bushing 460 includes an aperture 462 extending longitudinally therethrough. Aperture 462 is dimensioned and configured to allow a portion of control rod 52 to longitudinally slide therethrough. That is, bushing 460 is slidingly positioned about control rod 52.

Finger 480 of bushing 460 is configured to mechanically engage first link 402. In particular, tongue 482 of finger 480 is configured for reception at least partially within (or through) engagement structure 414 of first link 402. Additionally, finger 480 is configured to flex with respect to body portion 470. More specifically, finger 480 is able to move away from longitudinal axis "A." With particular reference to FIGS. 11 and 12, the flexibility of finger 480 facilitates the assembly of instrument 10, e.g., locking mechanism 400. That is, during assembly, proximal movement of first link 402 (shown at an angle with respect to the longitudinal axis "A") causes a proximal end 402b of first link 402 to engage tongue 482, and in particular an angled portion 483 thereof As shown, engagement between first link 402 and angled portion 483 of tongue 482 causes finger 480 to flex away from the longitudinal axis "A," thus allowing or facilitating continued proximal movement of first link 402. First link 402 is able to continue to advance proximally until proximal end 402b of first link 402 contacts a distal surface 474 of body portion 470 of bushing 460. Here, a proximal edge 414a of engagement structure 414 of first link 402 has moved proximally past tongue 482, thus allowing tongue 482 to move toward the longitudinal axis "A" (i.e., toward its biased position parallel with the longitudinal axis "A") and at least partially within engagement structure 414. In this position, first link 402 and bushing 460 are mechanically engaged, such that longitudinal movement of either of these two components causes a corresponding longitudinal movement of the other component. Further, the engagement between bushing 460 and first link 402 prevents longitudinal translation of first link 402 upon longitudinal translation of control rod 52.

The proximal end 402b of first link 402 is configured to contact (i.e., abuts or is axially movable into contact with) a distal surface 474 of body portion 470 of bushing 460. A proximal surface 476 of body portion 470 of bushing 460 is configured to contact (i.e., abuts or is axially movable into contact with) a distal end 406b of a wall of connecting tube 406. Accordingly, proximal movement of first link 402 causes corresponding proximal movement of bushing 460 and connecting tube 406, during loading of loading unit 500, for example. Similarly, distal movement of connecting tube 406 causes corresponding distal movement of bushing 460 and first link 402, during firing of the instrument, for example.

Additionally, the transverse dimension (i.e., along the y-axis in FIG. 8) of a contacting portion of the proximal surface 476 of body portion 470 of bushing 460 (i.e., the portion of bushing 460 illustrated above control rod 52 in FIG. 10) is between about 2 to about 10 times larger than the distal end 406b of a wall of connecting tube 406, and the transverse dimension (i.e., along the y-axis in FIG. 8) of a contacting portion of the distal surface 474 of body portion 470 of bushing 460 is between about 1 to about 3 times larger than the proximal end 402b of first link 402. Thus, as can be appreciated, bushing 460 provides a robust engagement between first link 402 and connecting tube 406. It is further envisioned that a surgical instrument without bushing 460 can be modified (e.g., by shortening the length of first link 402 (e.g., adjacent its proximal end 402b) and/or by shortening the length of connecting tube 406 (e.g., adjacent its distal end 406b)) to accommodate the disclosed bushing 460.

Figure 8:
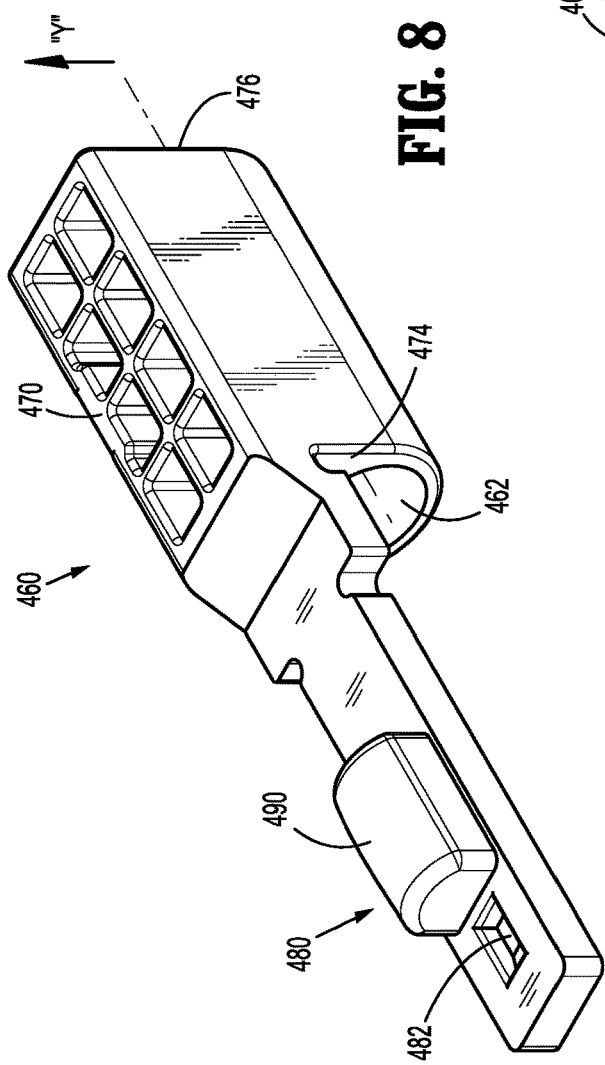
FIG. 8 is a perspective view of a bushing shown in FIG. 7.
Figure 9:
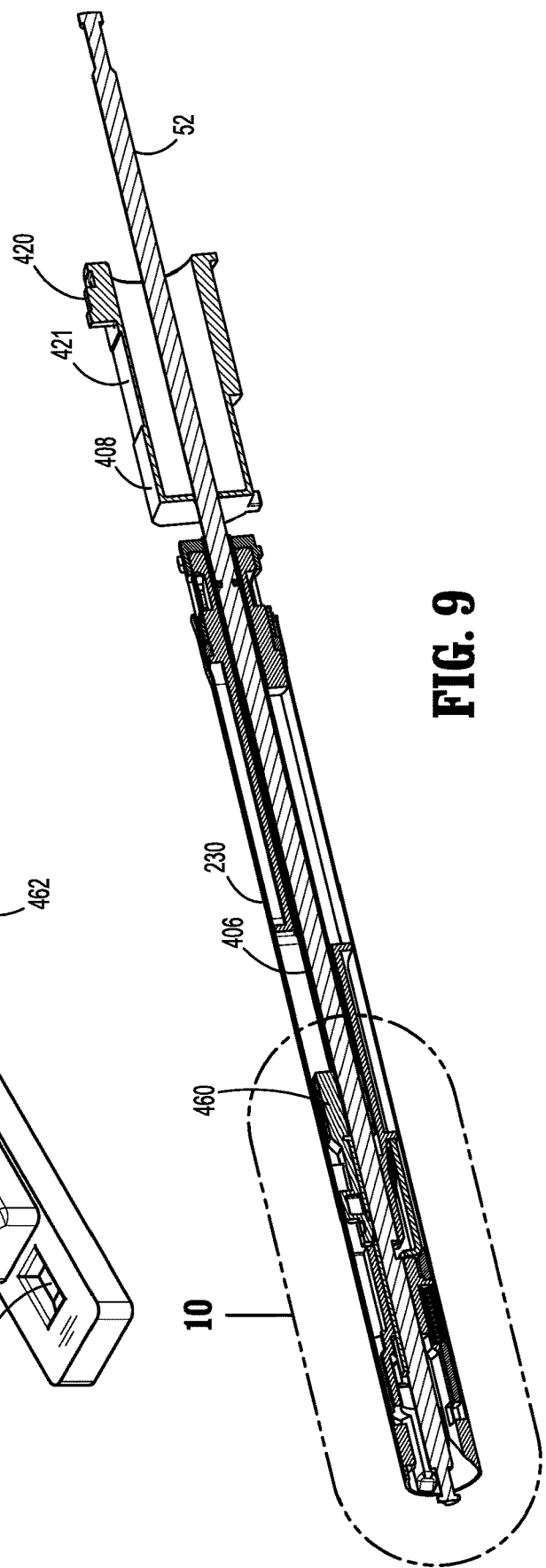
FIG. 9 is a cut-away perspective view of the locking mechanism taken along line 9-9 of FIG. 4.
Figure 10:
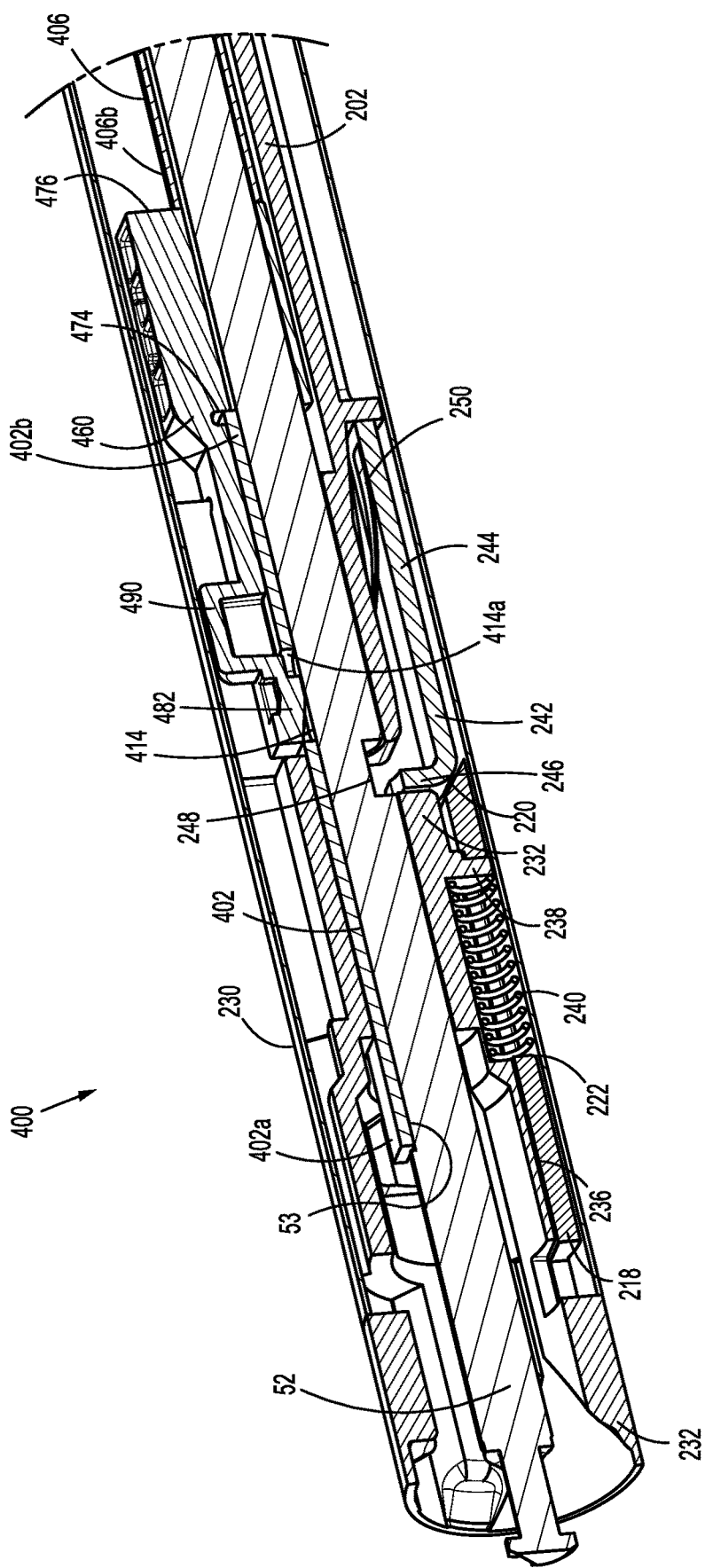
FIG. 10 is an enlarged view of the indicated area of detail shown in FIGS. 9.

Further, with reference to FIGS. 8 and 10, bushing 460 includes a step 490 disposed on finger 480. When instrument 10 is assembled (e.g., after outer tube 230 is slid over remainder of locking mechanism 400), step 490 is configured to abut or approximate an inner surface of outer tube 230. The limited space (or lack of space) between step 490 and the inner surface of outer tube 230 limits the amount of transverse travel that is possible between bushing 460 and outer tube 230. Thus, step 490 helps ensure finger 480 does not flex away from control rod 52 during use of instrument 10. Additionally, step 490 helps ensure engagement between tongue 482 and engagement structure 414 of first link 302.

Figure 6:
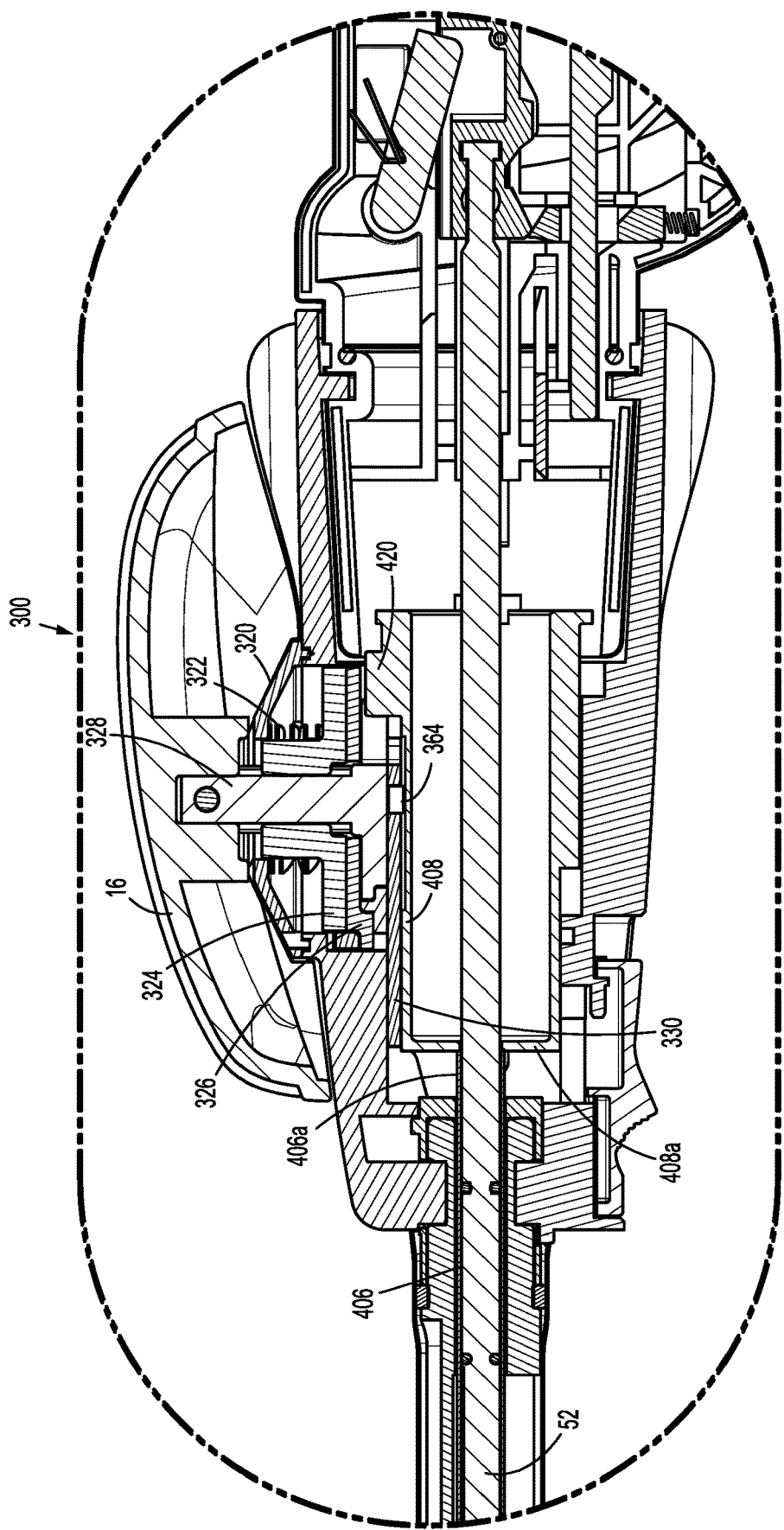
FIG. 6 is a longitudinal cross-sectional view of a portion of the surgical instrument.

With particular reference to FIG. 6, connecting tube 406 is slidably positioned about control rod 52 and has a proximal end 406a which abuts a distal face 408a of locking member 408. Locking member 408 is also slidably positioned about control rod 52. When bushing 460 and connecting tube 406 are moved proximally by first link 402 (e.g., when loading unit 500 is being loaded), locking member 408 is also moved proximally to allow distal translation of control rod 52. Further details of features and the operation of related surgical instruments are disclosed in commonly-owned U.S. patent application Ser. No. 13/274,497 filed on Oct. 17, 2011, the entire contents of which are hereby incorporated by reference herein.

With continued reference to FIG. 6, articulation mechanism 300 is illustrated and is configured to articulate an articulatable loading unit. Although loading unit 500 (FIG. 1) is not shown including articulation features, it is envisioned that loading unit 500 is articulatable in response to rotation of an articulation lever 16. Alternatively, instrument 10 may be configured as a cross-compatible device that is usable with articulating loading units as well as non-articulating loading units. When used with a non-articulating loading unit, articulation assembly 300 would simply be inoperable.

Articulation mechanism 300 includes articulation lever 16, a mechanism cover 320, biasing members 322, an upper clutch 324, a lower clutch 326, a main shaft 328, and a translation member 330. Lower clutch 326 is rotatably fixed and defines a central throughbore which is dimensioned to receive main shaft 328. Upper clutch 324 is rotatably fixed to main shaft 328 and includes a plurality of spaced projections which are received within serrations of lower clutch 326. Biasing members 322 urge upper clutch 324 into engagement with lower clutch 326 to releasably secure articulation mechanism 300 in a fixed position and, thus, to releasably secure the articulatable loading unit at a fixed angle of articulation.

Main shaft 328 includes a cam member 364, which is configured for sliding reception within a cam slot of translation member 330. When articulation lever 16 is rotated, cam member 364 is rotated about an axis defined by main shaft 328. When cam member 364 is driven in rotation, translation member 330 is urged to move linearly. Translation member 330 is configured to engage an articulation link 333 (FIG. 7) of an articulatable loading unit such that linear movement of translation member 330 effects linear movement of the articulation link 333 to effect articulation of the articulatable loading unit.

Figure 7:
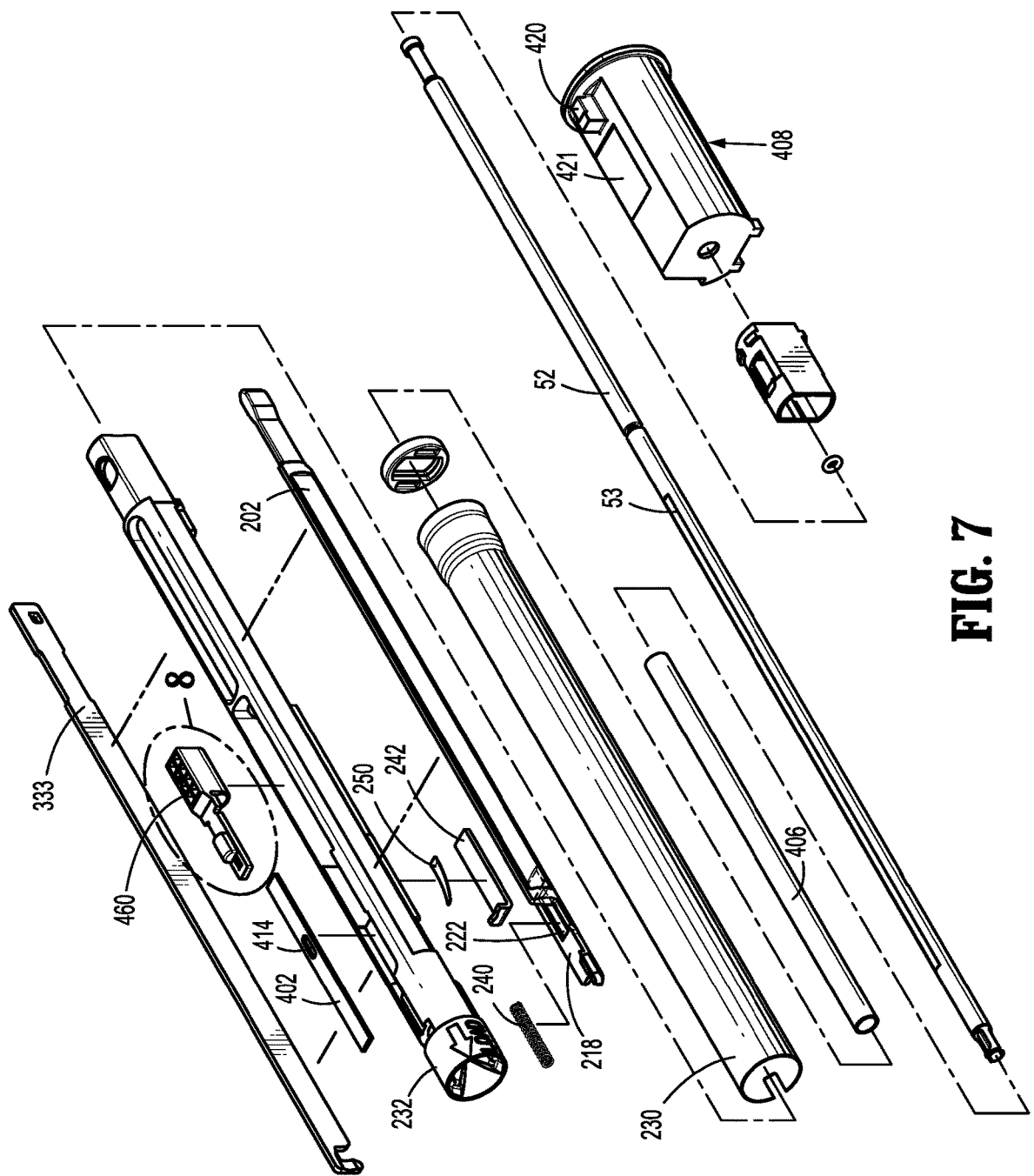
FIG. 7 is a perspective view of the elongated body portion of the surgical instrument shown with parts separated.

Referring to FIGS. 7 and 10, elongated body portion 30 of instrument 10 includes an outer tube 230 and an inner body portion 232 through which control rod 52 is inserted. Inner body 232 defines a recess 236 (FIG. 10) for slidably receiving release link 202 such that release link is slidably positioned between outer tube 230 and inner body portion 232. A projection 238 extending radially outwardly from body 232 extends into rectangular opening 222 of transverse extension 218 of release link 202 (FIG. 7). A spring 240 is positioned within rectangular opening 222 between projection 238 and a distal end of opening 222 to urge release link 202 distally.

Figure 2:
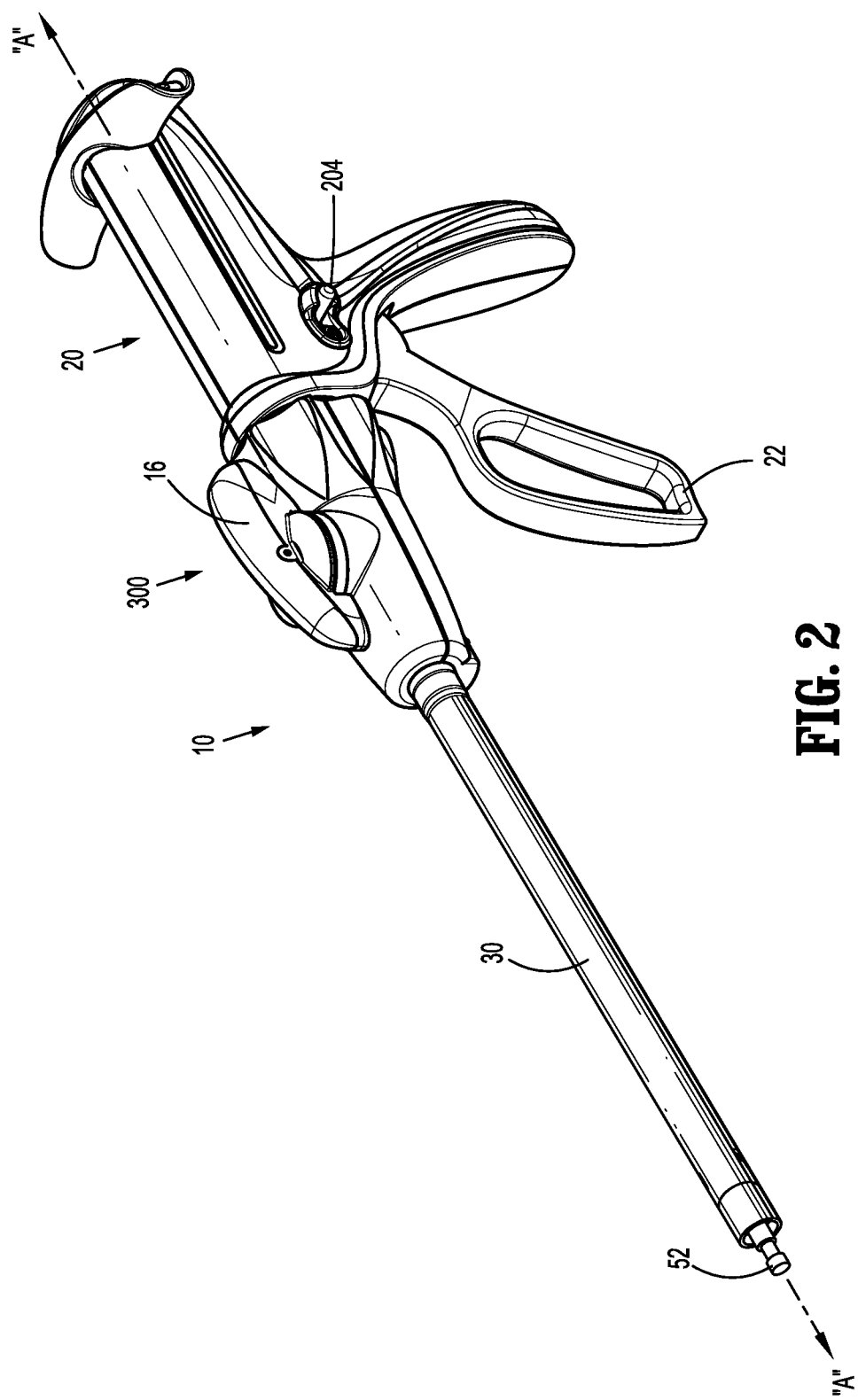
FIG. 2 is a perspective view of the surgical instrument without the loading unit engaged with the elongated body.
Figure 3:
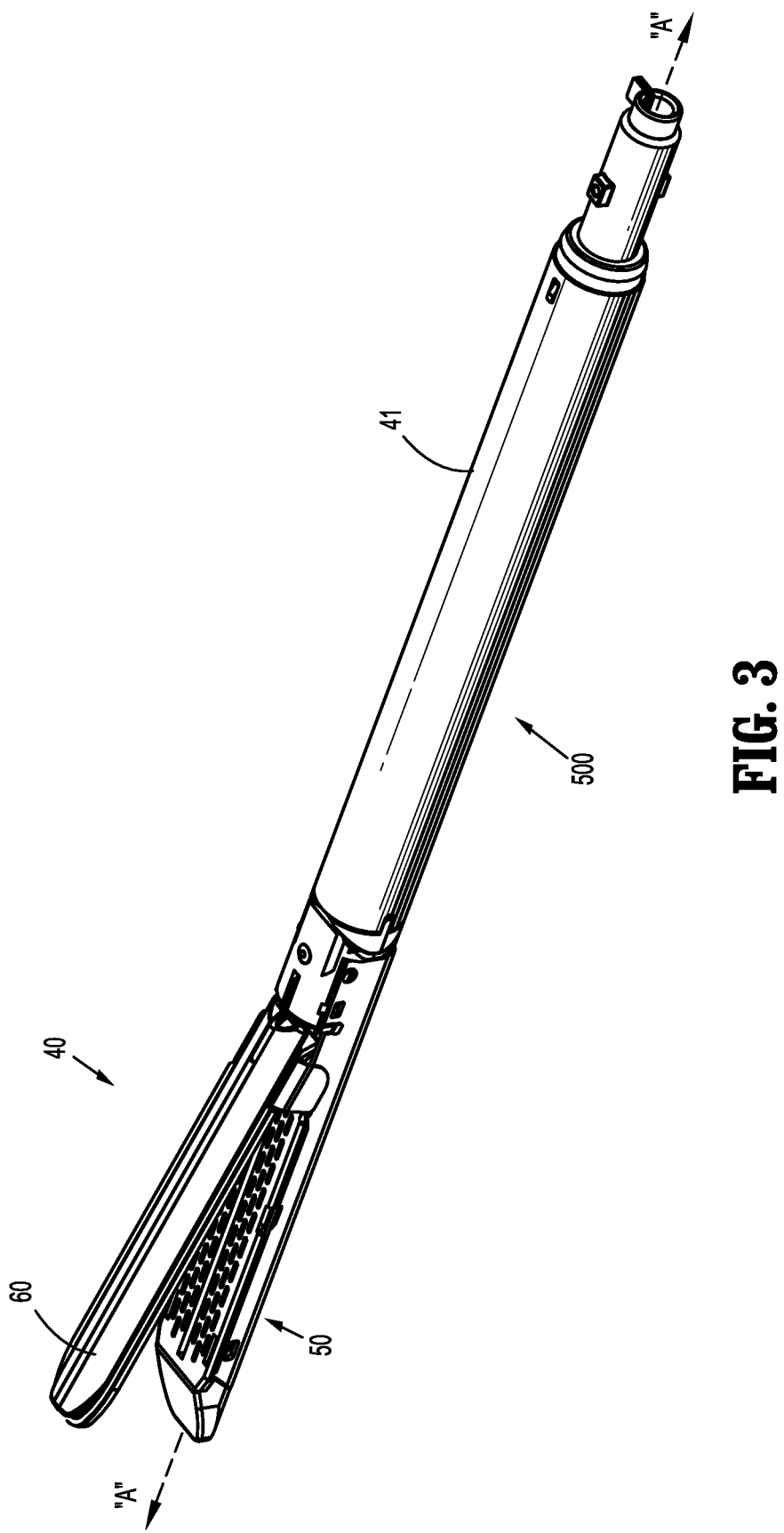
FIG. 3 is a perspective view of the loading unit.
Figure 4:
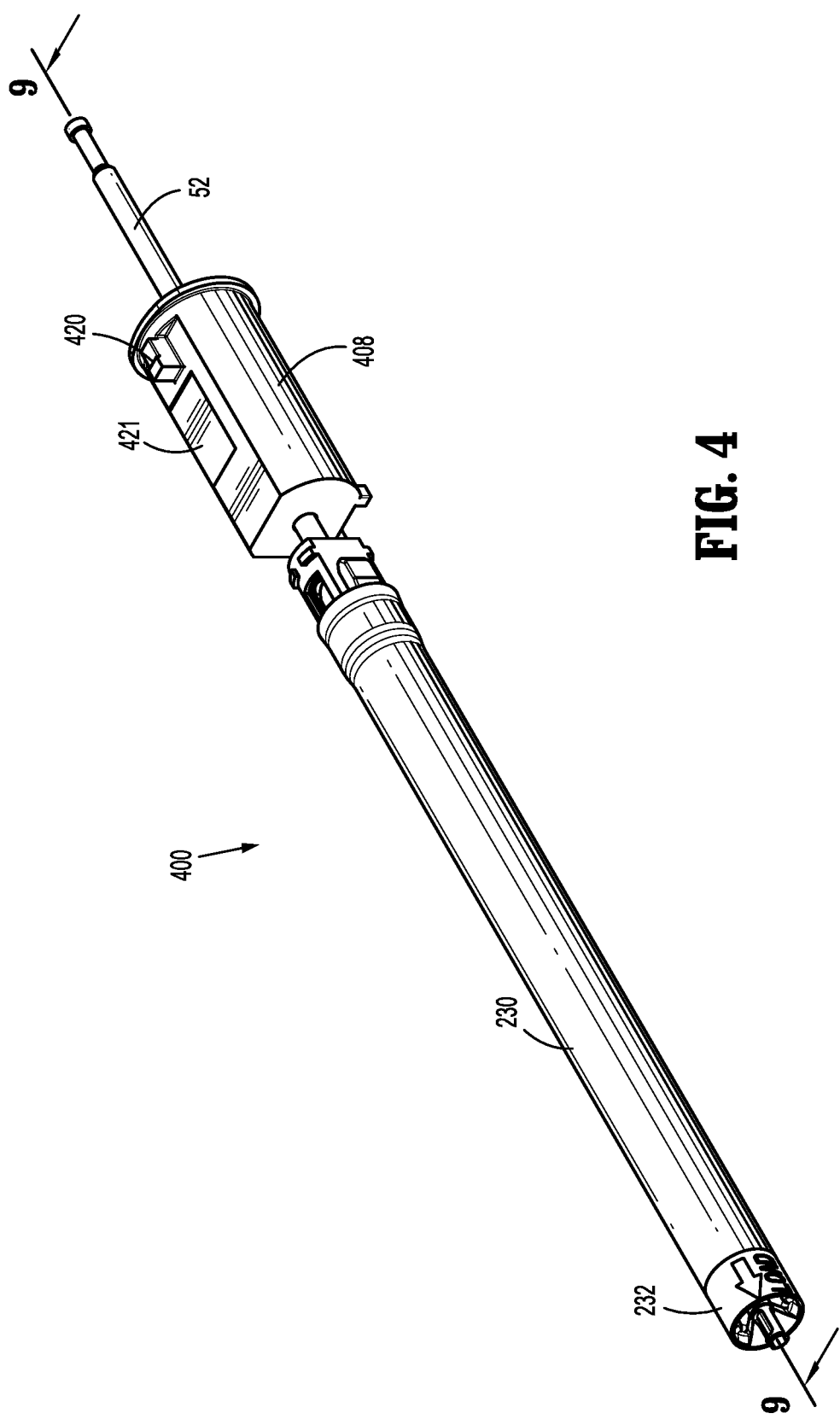
FIG. 4 is a perspective view of a locking mechanism of the surgical instrument.
Figure 5:
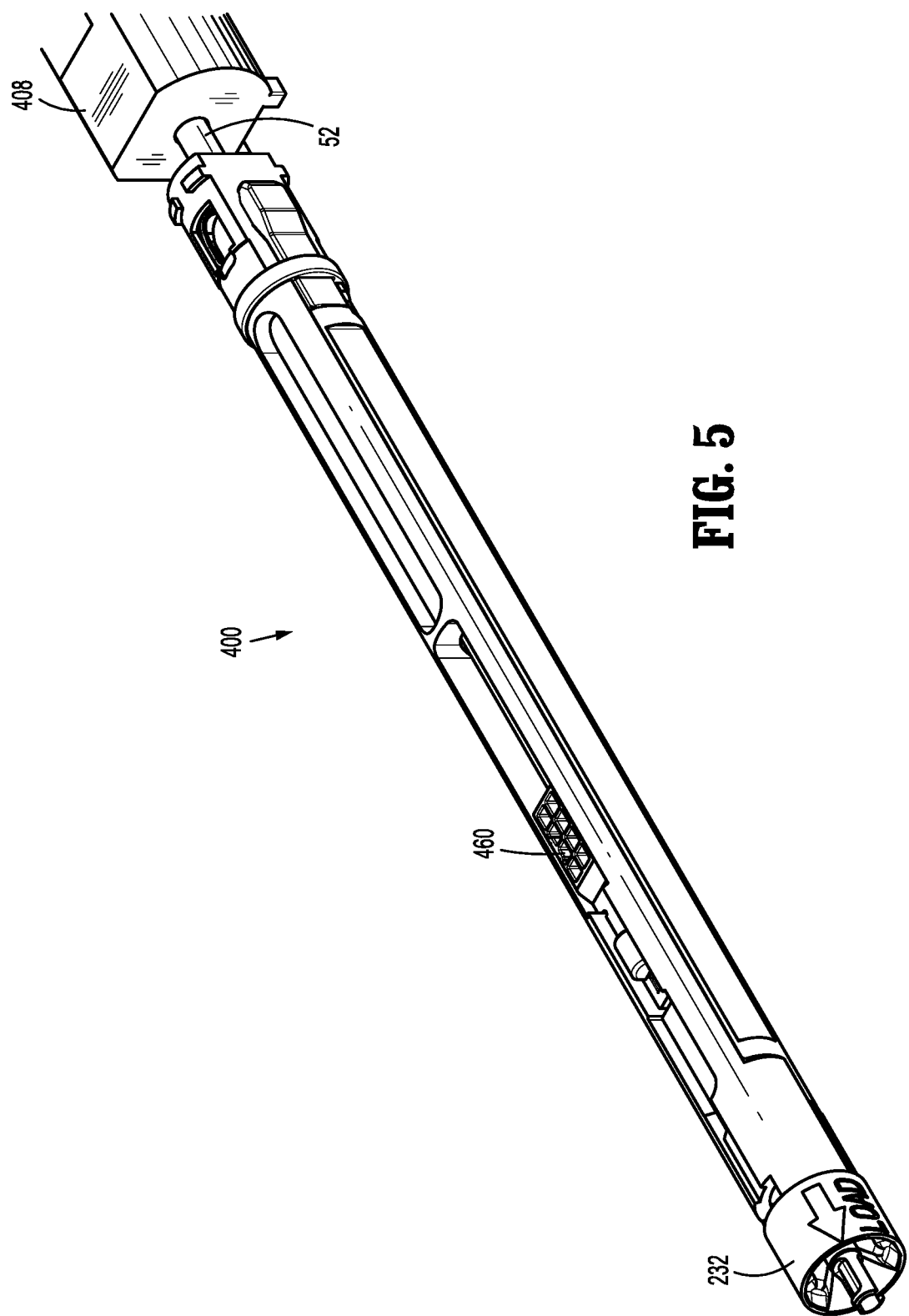
FIG. 5 is a perspective view of a portion of the locking mechanism of FIG. 4.

Hook 242 is positioned between outer tube 230 and inner body portion 232 adjacent a ramped cam surface 220. Hook 242 includes an elongated body 244 having a transverse distal end 246. Transverse distal end 246 is positioned adjacent a cutout 248 in control rod 52. Hook 242 is urged by a biasing member 250 to a position in which distal end 246 of hook 242 is located externally of cutout 248. When release link 202 is moved proximally against the urging of biasing member 240 (e.g., by pulling a release button 204 (FIGS. 1 and 2) proximally), cam surface 220 moves distal end 246 of hook 242 into cutout 248 of control rod 52. If control rod 52 is not in its retracted position shown in FIG. 10 and notch 248 is not positioned to receive distal end 246 of hook 242, cam surface 220 will not be able to cause hook 242 to move radially inwardly and thus link 202 will not be able to move proximally. Thus, a loading unit 500 cannot be removed or installed if control rod 52 is not in the retracted position.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A locking mechanism for use with a surgical instrument, comprising:
    a link disposed in a tubular member and configured for longitudinal movement therein;
    a bushing having a body portion and a finger extending distally therefrom, a portion of the bushing disposed proximally of the link and longitudinally translatable with respect to the tubular member, the finger including a tongue configured to engage a portion of the link; and
    a connecting member, a portion of the connecting member disposed proximally of the bushing, the connecting member positionable in the tubular member and longitudinally translatable therein,
    wherein engagement of a loading unit with the tubular member causes proximal movement of the link, the bushing, and the connecting member.

2. The locking mechanism of claim 1, wherein a portion of the bushing is positioned radially between the tubular member and the link.

3. The locking mechanism of claim 1, wherein the body portion of the bushing includes an aperture extending longitudinally therethrough.

4. The locking mechanism of claim 1, wherein the finger of the bushing is configured to flex towards a wall of the tubular member.

5. The locking mechanism of claim 4, wherein engagement between the link and an angled portion of the tongue causes the finger to flex towards the wall of the tubular member.

6. The locking mechanism of claim 1, wherein the bushing includes a step disposed on the finger.

7. The locking mechanism of claim 1, wherein distal movement of the connecting member causes corresponding distal movement of the bushing and the link.

8. The locking mechanism of claim 1, wherein the tubular member is a shaft of a surgical instrument, the shaft extending from a housing of the surgical instrument.

9. The locking mechanism of claim 8, further including a control rod disposed at least partially within the tubular member, wherein longitudinal translation of the control rod effects a function of the loading unit when the loading unit is engaged with the tubular member.

10. The locking mechanism of claim 9, wherein the control rod is longitudinally translatable with respect to the link, the bushing, and the connecting member.

11. The locking mechanism of claim 9, wherein the control rod is longitudinally translatable through an aperture of the bushing.

12. A locking mechanism for use with a surgical instrument, comprising:
    a release link disposed within a tubular member, a portion of the release link being longitudinally translatable with respect to the tubular member;
    a bushing including a finger and a tongue, the tongue configured to engage a portion of the release link, wherein at least a portion of the bushing is disposed proximally of the release link; and
    a connecting member, a portion of the connecting member disposed proximally of the bushing, the connecting member positionable in the tubular member and longitudinally translatable therein, such that distal movement of the connecting member causes corresponding distal movement of the bushing and the release link.

13. The locking mechanism of claim 12, wherein the bushing is located radially between the tubular member and the release link.

14. The locking mechanism of claim 12, further including an aperture extending longitudinally through a body portion of the bushing.

15. The locking mechanism of claim 12, further including a flexible finger configured to flex towards a wall of the tubular member.

16. The locking mechanism of claim 15, wherein the flexible finger includes a step disposed thereon.

17. The locking mechanism of claim 12, wherein distal movement of the connecting member causes corresponding distal movement of the bushing and the release link.

18. The locking mechanism of claim 12, further including a control rod longitudinally translatable with respect to the release link, the bushing, and the connecting member.

19. The locking mechanism of claim 12, wherein the release link includes an opening configured to engage a portion of the tongue.

20. A locking mechanism for use with a surgical instrument, comprising:
    a link disposed in a tubular member and configured for longitudinal movement therein;
    a bushing having a body portion and a finger extending distally therefrom, the body portion including an aperture extending longitudinally therethrough, a portion of the bushing disposed proximally of the link and longitudinally translatable with respect to the tubular member, the finger including a tongue configured to engage a portion of the link; and
    a connecting member, a portion of the connecting member disposed proximally of the bushing, the connecting member positionable in the tubular member and longitudinally translatable therein,
    wherein engagement of a loading unit with the tubular member causes proximal movement of the link, the bushing, and the connecting member.

* * * * *